(12) United States Patent
Reichert

(10) Patent No.: US 8,016,417 B2
(45) Date of Patent: Sep. 13, 2011

(54) EYE MODEL

(76) Inventor: Abraham Reichert, Modiin (IL)

( * ) Notice: Subject to any disclaimer, the term of this patent is extended or adjusted under 35 U.S.C. 154(b) by 97 days.

(21) Appl. No.: 12/496,714

(22) Filed: Jul. 2, 2009

(65) Prior Publication Data

US 2010/0002311 A1    Jan. 7, 2010

Related U.S. Application Data

(60) Provisional application No. 61/077,490, filed on Jul. 2, 2008.

(51) Int. Cl.
*A61B 3/00* (2006.01)
*G02B 9/06* (2006.01)
*G09B 23/28* (2006.01)

(52) U.S. Cl. .................. 351/200; 359/794; 434/271

(58) Field of Classification Search .................. 351/200, 351/205, 219; 359/794; 434/271
See application file for complete search history.

(56) References Cited

U.S. PATENT DOCUMENTS

| | | | | |
|---|---|---|---|---|
| 4,932,764 A * | 6/1990 | Simpson, Jr. | ................ | 359/725 |
| 5,000,552 A * | 3/1991 | Simpson et al. | ............. | 359/740 |
| 5,677,798 A * | 10/1997 | Hirano et al. | ................ | 359/717 |
| 6,626,535 B2 * | 9/2003 | Altmann | ....................... | 351/177 |
| 7,031,080 B2 * | 4/2006 | Koike | .......................... | 359/794 |
| 7,066,598 B2 * | 6/2006 | Niven | .......................... | 351/205 |
| 7,684,129 B1 * | 3/2010 | Wang et al. | ................... | 359/794 |

* cited by examiner

*Primary Examiner* — Jordan M. Schwartz
(74) *Attorney, Agent, or Firm* — Dekel Patent Ltd.; David Klein

(57) ABSTRACT

An eye model including a front positive lens, a rear positive lens, an aperture stop located between the front and rear positive lenses, and a focal plane located rearward of the rear positive lens, wherein the front positive lens has a meniscus shape having an outer surface radius equal to a radius of a human eye, and wherein the rear positive lens has a rear surface having a radius equal to a distance from the aperture stop to the rear surface.

2 Claims, 8 Drawing Sheets

EYE MODEL

CROSS-REFERENCE TO RELATED APPLICATIONS

This application claims priority under 35 USC §119 to U.S. Provisional Patent Application, Ser. No. 61/077,490, filed Jul. 2, 2008, which is incorporated herein by reference.

FIELD OF THE INVENTION

The present invention relates generally to an eye model, and particularly to an eye model for measurement by an ophthalmic diagnostic instrument for calibration and development purposes.

BACKGROUND OF THE INVENTION

A difficulty in the development of ophthalmic diagnostic devices is obtaining information about the human eye, such as geometry, aperture diameter depth, etc. without incurring significant discomfort or injury to a human subject. The development of an ophthalmic diagnostic instrument requires repetitive gathering of information, and this can be painful and problematic for a human test subject.

An additional problem is the fact that the eye is a living organism and differs from one person to the next. Obviously, this compounds the problem of gathering accurate data about the eye geometry because there is no way to truly measure in-vivo tissue of the eye to the micron level without physically removing the eye.

SUMMARY OF THE INVENTION

The present invention seeks to provide a new eye model which overcomes the drawbacks mentioned above of the prior art. The eye model has no fluid and yet simulates the optical performance of the human eye, as is described more in detail hereinbelow.

BRIEF DESCRIPTION OF THE DRAWINGS

The present invention will be understood and appreciated more fully from the following detailed description taken in conjunction with the appended drawings in which.

DETAILED DESCRIPTION OF THE PRESENT INVENTION

Reference is now made to FIG. 1A, which illustrates a schematic view of a stereotactic radiotherapy system 10 with a rotating attenuator 12, constructed and operative in accordance with an embodiment of the present invention.

Figure 1:
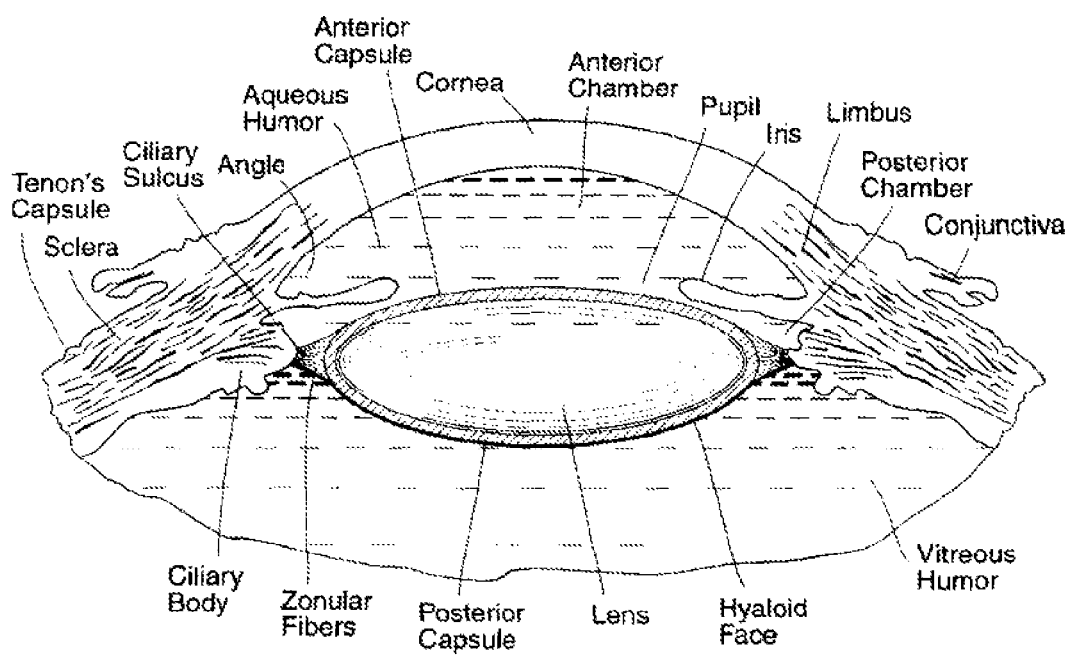
FIG. 1 is a model of a human eye.

FIG. 1 illustrates various parts of the human eye, e.g., zonular fibers, posterior chamber, iris, pupil, cornea, anterior chamber (that has aqueous humor), ciliary muscle, and others.

Figure 2:
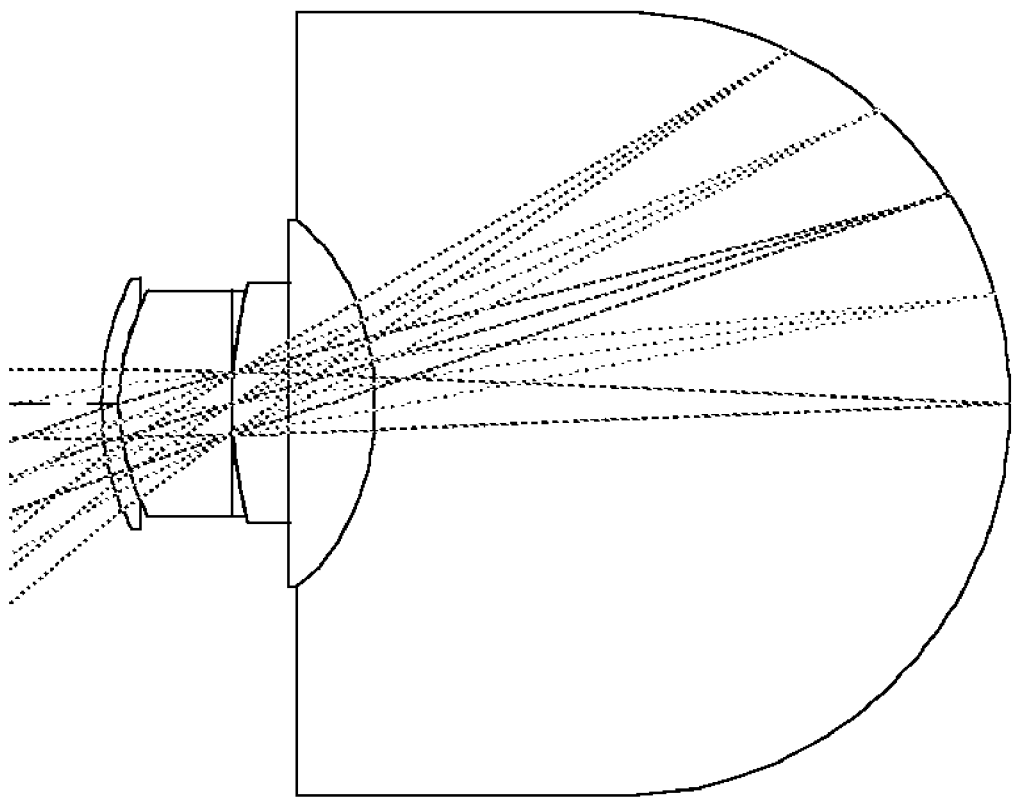
FIG. 2 is a schematic optical model of an eye, proposed by Liou and Brennan (1977) "Anatomically accurate, finite model eye for optical modeling", *J. Opt. Soc. Am A*, 14, 1684-95.
Figure 3:
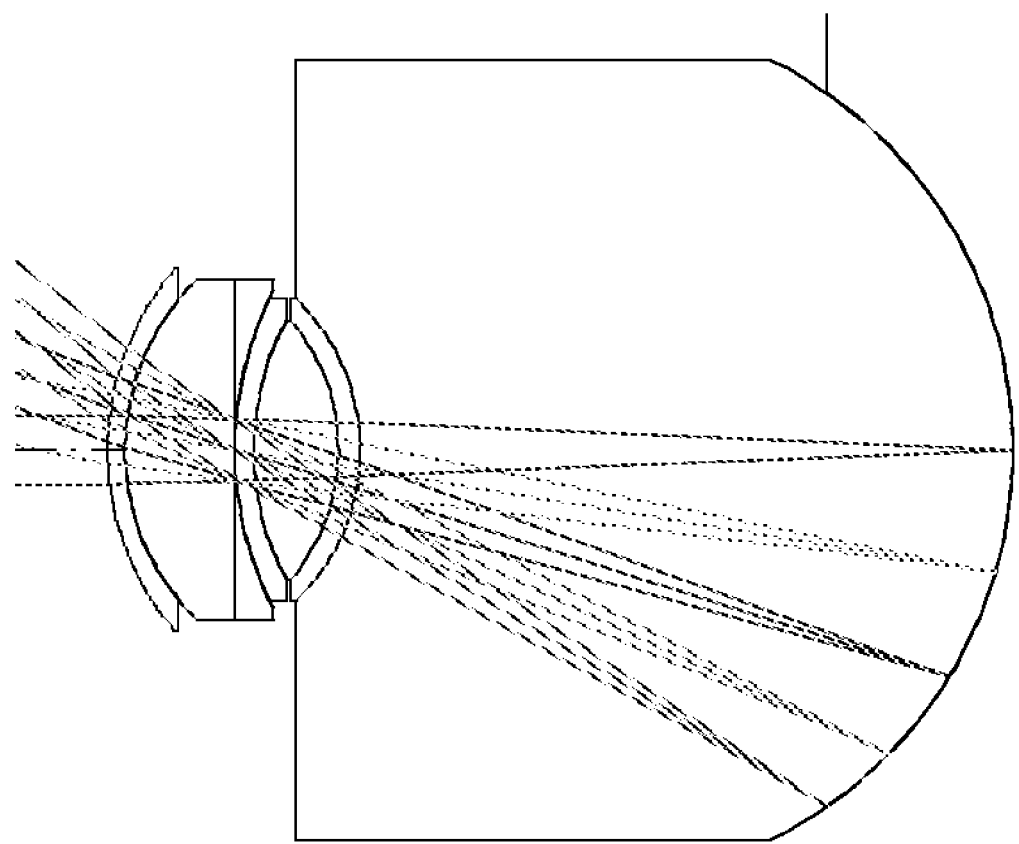
FIG. 3 is a schematic optical model of an eye, proposed by Optical Research and Associates.

FIG. 2 shows the schematic drawing of an eye as been investigated and published by Liou and Brennan. This model represents the real curvatures, dimensions and material of a normal human eye. Another model is described in FIG. 3, by ORA according to the Handbook of Optics.

Figure 4:
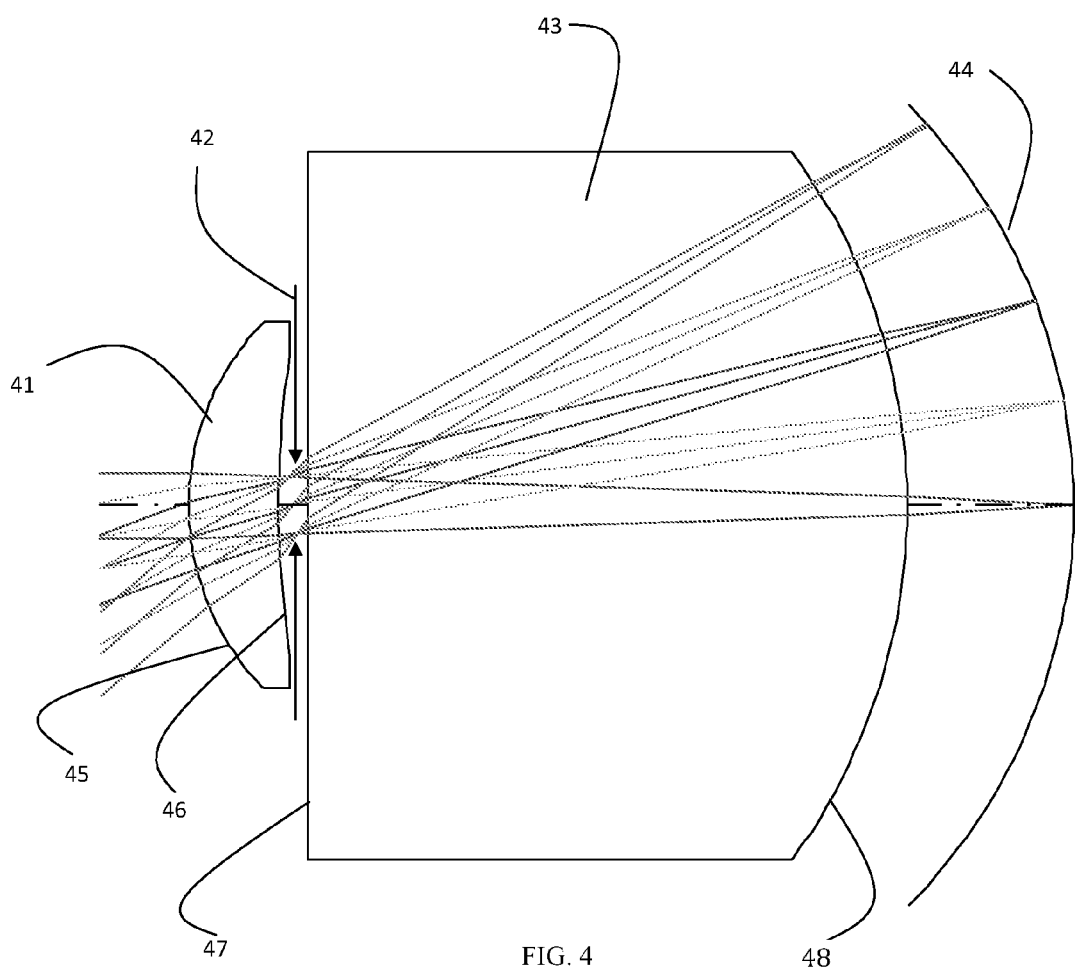
FIG. 4 is a perspective view of an eye model in accordance with an embodiment of the present invention.

FIG. 4 illustrates an eye model in accordance with an embodiment of the present invention. The eye model includes a front positive lens 41, an aperture stop 42, a rear positive lens 43 and a focal plane 44. The front positive lens 41 has a meniscus shape having an outer surface radius 45 of the same radius of a normal human eye (e.g., about 7.8 mm). The power of the front positive lens is 80-90% of the total power of the eye module. The aperture stop 42 is located between the front positive lens 41 and the rear positive lens 43, and determines the ray cone angle, or equivalently the brightness, at an image point. The rear positive lens 43 has a rear surface 48, which has an absolute value of its radius equal or equivalent to the distance of the rear surface of lens 43 from the aperture stop 42, so as to create a concentric surface with respect to the aperture stop location.

Figure 5:
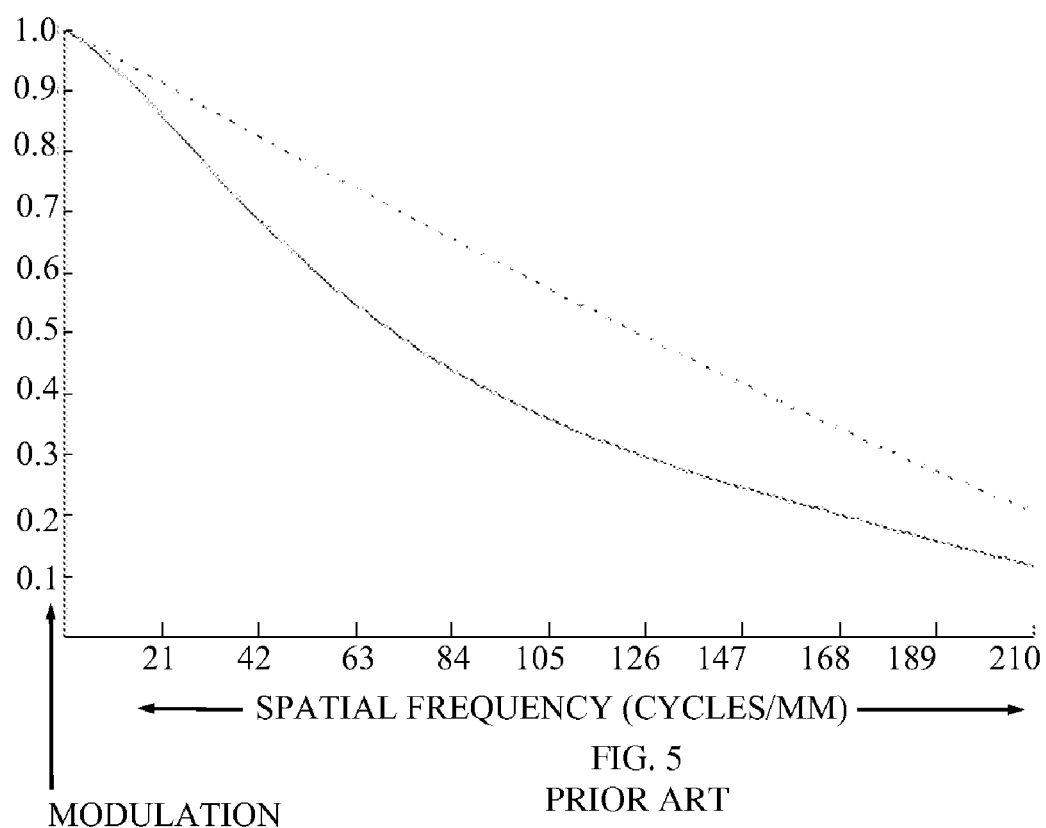
FIG. 5 is the optical modulation transfer function (MTF) of a human eye at a pupil of 3 mm of the Liou and Brennan model.
Figure 6:
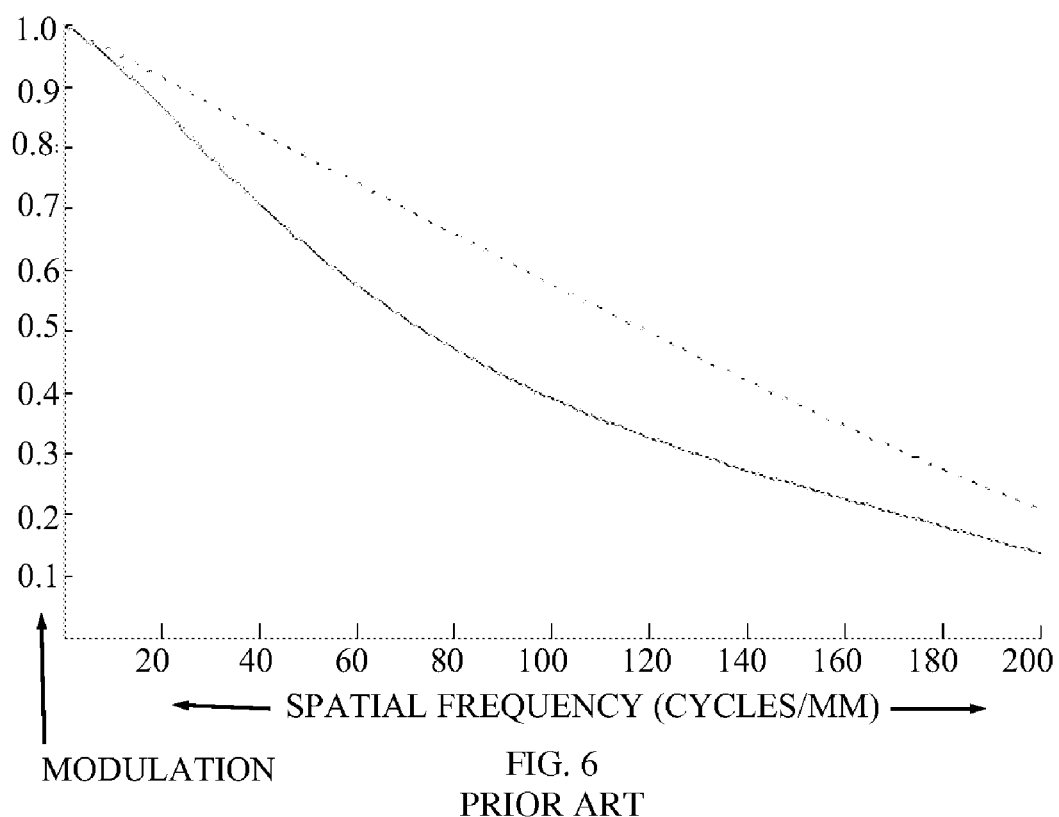
FIG. 6 is the MTF at pupil of 3 mm of the Optical Research and Associates model.
Figure 7:
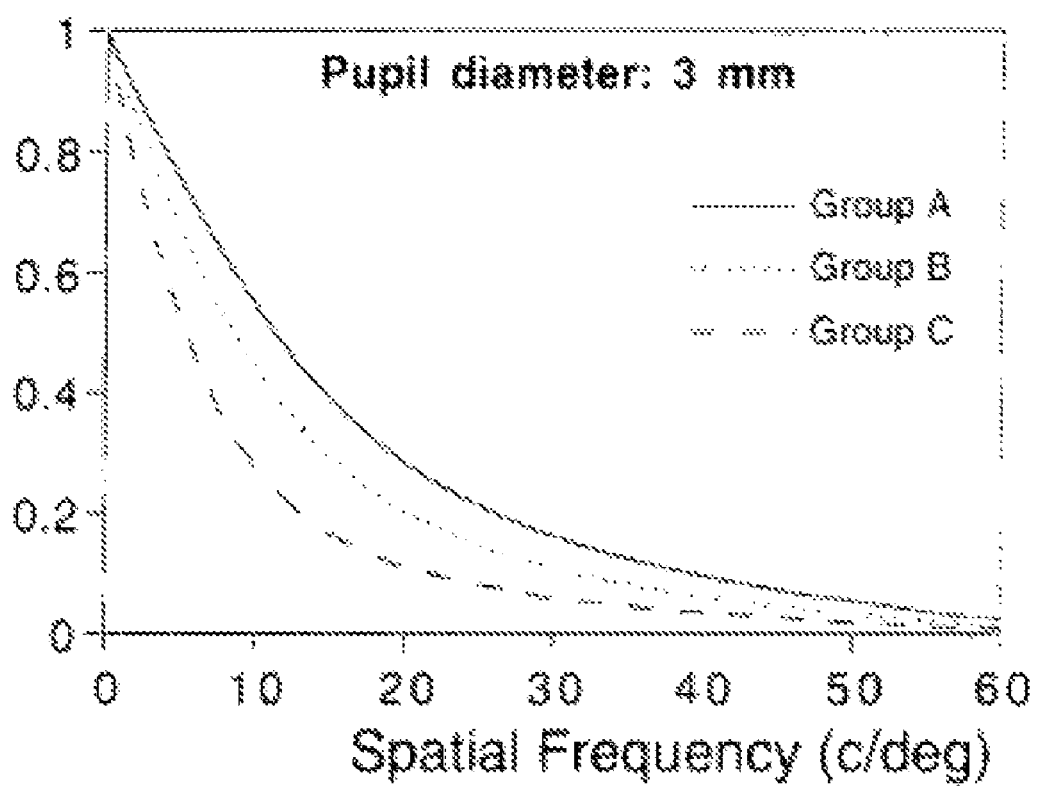
FIG. 7 is the MTF at pupil of 3 mm measured on a real human eye.
Figure 8:
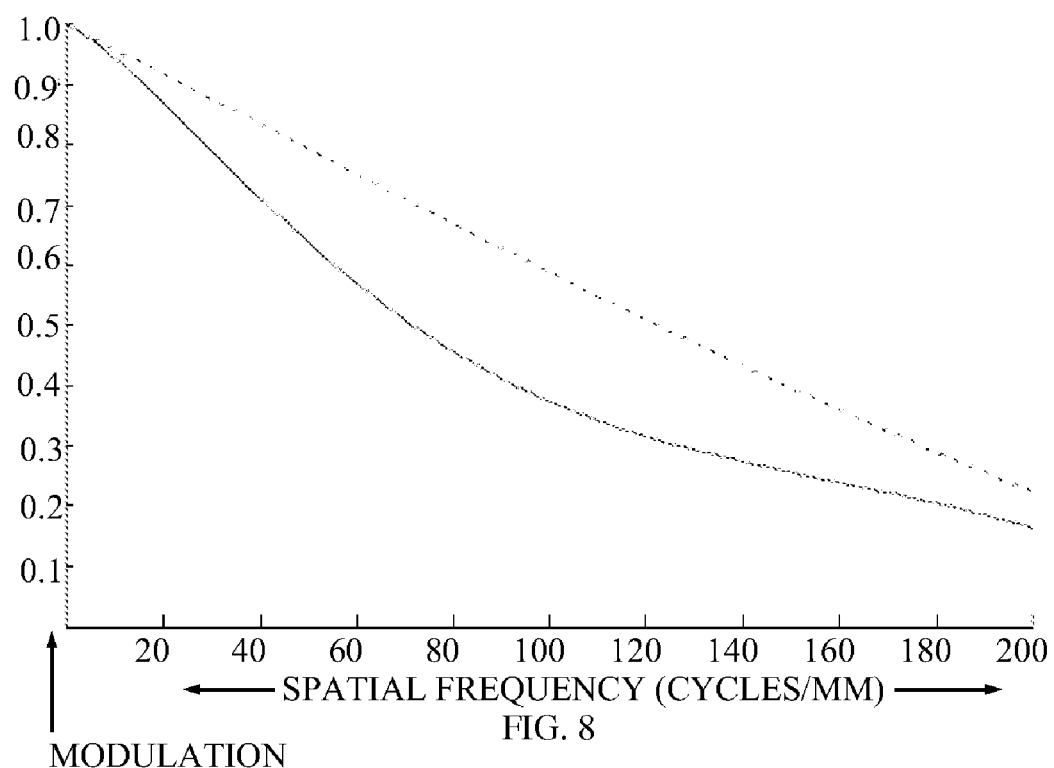
FIG. 8 is the MTF at pupil of 3 mm of the eye model of an embodiment of the present invention.

The MTF results of the eye model lens can be show in FIG. 8, and it can be seen that it is equal to the MTF of the two model eyes of FIGS. 5 and 6 and the eye of FIG. 7.

It will be appreciated by persons skilled in the art that the present invention is not limited by what has been particularly shown and described hereinabove. Rather the scope of the present invention includes both combinations and subcombinations of the features described hereinabove as well as modifications and variations thereof which would occur to a person of skill in the art upon reading the foregoing description and which are not in the prior art.

What is claimed is:

1. An eye model comprising:
   a front positive lens;
   a rear positive lens;
   an aperture stop located between said front and rear positive lenses; and
   a focal plane located rearward of said rear positive lens, wherein said front positive lens has a meniscus shape having a frontward outer surface radius equal to about 7.8 mm, and wherein said rear positive lens has a rear surface having an absolute value of its radius equal to a distance from said aperture stop to said rear surface.

2. An eye model comprising:
   a front positive lens;
   a rear positive lens;
   an aperture stop located between said front and rear lenses; and
   a focal plane located rearward of said rear positive lens, wherein said front positive lens has a meniscus shape having an outer surface radius equal to about 7.8 mm, and wherein said rear positive lens has a rear surface having an absolute value of its radius equal to a distance from said aperture stop to said rear surface, and wherein a power of the front positive lens is 80-90% of the total power of the eye module.

* * * * *